United States Patent
Buyayez

[19]

[11] Patent Number: 5,640,786
[45] Date of Patent: Jun. 24, 1997

[54] MONITORED FOOTWEAR WITH STEP COUNTER AND SPEEDOMETER DISPLAY

[76] Inventor: Taher Buyayez, 2302 Naples, Newport Beach, Calif. 92660-3257

[21] Appl. No.: 498,408

[22] Filed: Jul. 5, 1995

[51] Int. Cl.⁶ .............. A61B 9/00; A61B 5/103; A43B 5/00
[52] U.S. Cl. .............. 36/114; 36/132; 36/136; 73/172; 128/779
[58] Field of Search .............. 36/1, 114, 132, 36/136; 73/172; 128/779

[56] References Cited

U.S. PATENT DOCUMENTS

| | | | |
|---|---|---|---|
| 4,402,147 | 9/1983 | Wu | 36/136 |
| 4,466,204 | 8/1984 | Wu | 36/136 |
| 4,510,704 | 4/1985 | Johnson | 36/136 |
| 4,649,552 | 3/1987 | Yukawa | 36/132 |
| 4,814,661 | 3/1989 | Ratzlaff et al. | 36/136 |
| 4,891,797 | 1/1990 | Woodfalks | 36/132 |
| 5,373,651 | 12/1994 | Wood | 36/136 |

*Primary Examiner*—M. D. Patterson
*Attorney, Agent, or Firm*—G. Donald Weber, Jr.

[57] ABSTRACT

Articles of footwear including a power supply, a logic circuit, at least two pressure switches which control the operation of the logic circuit, a counter circuit, a monitor circuit, a driver circuit and a display device. The counter circuit counts all such steps and determines use of the footwear vis-a-vis life of the footwear and/or characteristics of the use of the footwear. The display device selectively displays the number of steps taken in the footwear, or the speed at which the steps were taken.

7 Claims, 1 Drawing Sheet

MONITORED FOOTWEAR WITH STEP COUNTER AND SPEEDOMETER DISPLAY

BACKGROUND

1. Field of the Invention

This invention relates to footwear, in general, and to footwear having electronic circuitry associated therewith for measuring parameters of usage of the footwear, in particular.

2. Prior Art

It has been previously known to provide footwear with constant illumination, or with intermittently flashing illumination. For example, see U.S. Pat. No. 4,158,922 to Dana. The device described in the Dana patent does not provide means for extinguishing the illumination, whether constantly on, or if merely intermittently flashing. That is, the Dana device uses a mercury switch as a control device. Mercury switches are position sensitive whereby the illumination will stay on (or continue flashing) if the attitude of the is mercury switch places it in "on" position.

An alternative device is described, for example, in U.S. Pat. No. 4,848,009 to Rodgers. In Rodgers there is provided a footwear with a light source located thereon so as to be visible from the exterior of the footwear. In the Rodgers' device, a power source, a light source, and a circuit for selectively energizing the light source are provided. The Rodgers' device also includes a switch designed to alternate between "off" and "on" states in response to motion of the footwear, as well as a timing circuit. The timing circuit is responsive to the transition of the switch from the "off" to the "on" state and operates to turn off the light source after a predetermined time period and to prevent the light source from being turned on again until a further transition of the switch has occurred.

In the previously known illuminated footwear, the light source is an incandescent light bulb or a light emitting device (LED). Obviously, the use of LED's produces a bright display in selected colors and requires much less energy than an incandescent ilumination, thus giving longer battery life.

SUMMARY OF THE INSTANT INVENTION

This invention is directed to an electronic circuit to be used with footwear such as a shoe or running shoe, for example. The electronic circuitry is designed to detect parameters of usage of the footwear. The circuitry is mounted within the shoe. The usage can be measured in terms of either the number or the speed of steps taken by the wearer of the footwear. The circuitry detects walking or running parameters as a function of the operation of two pressure sensitive switches in the bottom of the footwear. The parameters are displayed on a display device connected to the footwear. The display can be controlled to indicate the number of steps taken or the rate at which the steps were taken, or both.

DESCRIPTION OF A PREFERRED EMBODIMENT

Figure 1:
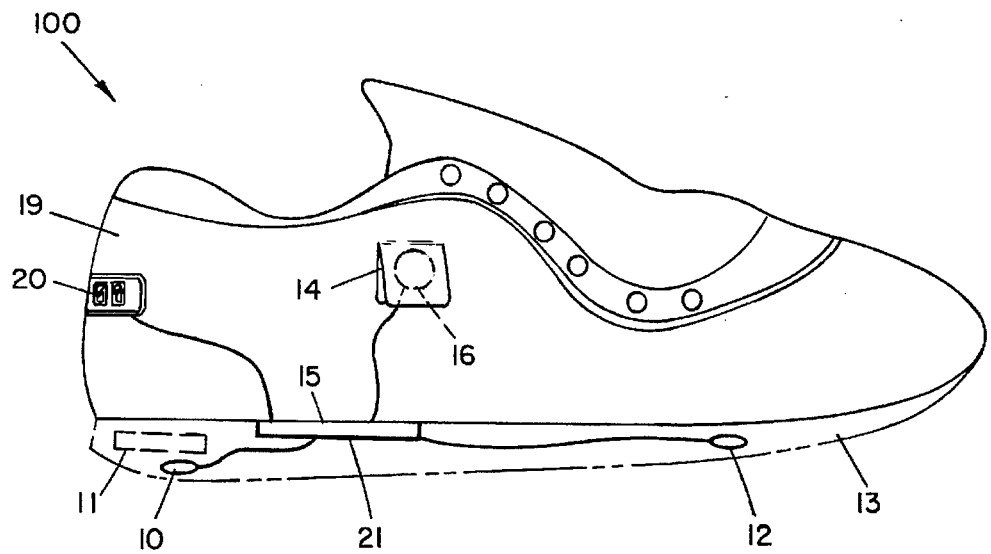
FIG. 1 shows a representation of a running shoe in accord with the invention schematically showing some circuit components in place.

Referring now to FIG. 1, there is shown a representation of a typical footwear 100 such as a sports shoe, a running shoe or the like. Pressure switches 10 and 12 are, preferably, encapsulated in the heel 11 and sole 13, respectively, of shoe 100 during manufacture. (Rotary switches can be used for wheeled footwear, such as rollerskates or the like.)

Operational circuitry 15 is formed of any conventional integrated or microcircuit techniques. The circuitry 15 can be mounted in shoe 100 in any convenient location. As shown in FIG. 1, a convenient location for placement of the circuitry 15 is in the arch support area between the sole 13 and the heel 11. In a preferred embodiment, the circuitry 15 is included in the "bottom" of the shoe during the manufacturing process. A location with as little flexure or stress is preferred. Of course, the circuitry 15 can be mounted at any suitable place in the shoe 100.

Switches 10 and 12 are connected to circuitry 15 by suitable connectors (or conductors) which are imbedded in the shoe 100. The switches 10 and 12 are pressure switches which selectively operate the circuitry 15 as described hereinafter. It will be understood that switches 10 and 12, battery 16, and circuitry 15 may be located in the shoe 100 as indicated in FIG. 1. The integrated circuitry 15, the switches 10 and 12 and the remainder of the elements shown in FIG. 1 are encapsulated in the material of the shoe, preferrably in the heel and sole, as shown.

Although it is preferred to encapsulate the switches 10 and/or 12 in the shoe, the switches can be attached to the exterior of the shoe, if desired. The switches will be designed to be "off" when the shoe is not in use and, thus, the switches are not pressurized.

A display 20 is shown mounted at the back 19 of shoe 100. The display is also connected to circuitry 15 and driven thereby. It is contemplated that the display can be an LCD (liquid crystal display) or the equivalent. The type of display is not limitative of the invention, per se. As will be apparent, the display 20 can be permanently or removably affixed to the back 19 of shoe 100.

A battery 16 is connected to circuitry 15 to provide the power therefor, as well as for the display 20. In one embodiment, the battery 16 is located in a pouch 14 or under a flap closable by a hook and loop fastener, or by other conventional means inside the shoe. The battery 16 is, preferably, connected to be easily disconnected, replaced, and reconnected to the shoe by conventional means. The battery 16 which may be of any conventional type is, preferably, of the lithium chloride type for long life.

Figure 2:
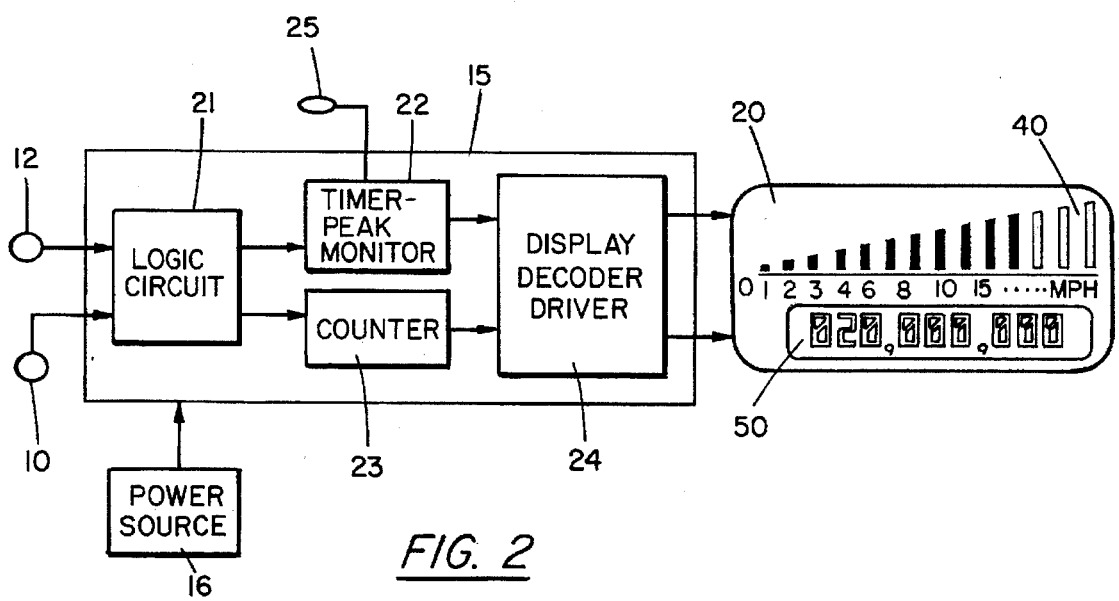
FIG. 2 shows a functional block diagram of the circuitry of the shoe of FIG. 1.

Referring now to FIG. 2, there is shown a block diagram of the circuitry 15. As shown in FIG. 2, the power source 16 (i.e. a battery) is connected to the circuitry 15 to provide power thereto. The switches 10 and 12 are connected to the logic circuit 21. As noted, the switches are pressure switches which are normally open and selectively closed by applying pressure thereto. Switches 10 and 12 may be a mechanical switch or a piezo-electric switch, as desired. Of course, other types of switches are contemplated, as well.

The outputs of logic circuit 21 are connected to timer/peak monitor 22 and counter 23, respectively. The outputs of the monitor 22 and counter 23 are connected to inputs of the decoder/driver 24. The output of decoder/driver 24 is connected to the input of display 20. The display 20 incorporates a speed indicator 40 and a step count indicator 50.

The speed indicator 40 is adapted to provide a display of the speed at which a wearer of the footwear is travelling. Typically, this indicator is calibrated in miles-per-hour (MPH).

The step count indicator 50 is adapted to provide a display of the number of steps taken by the wearer of the footwear.

Switch 25 is connected to the monitor 22. Switch 25 may be a pressure switch similar to the switches 10 and 12. Typically, switch 25 is mounted external to the shoe 100 and is a reset switch for the system.

In operation, with the shoe stationary, the switches 10, 12 and 25 will be open and the circuit quiescent. In addition, the display 20 will be, effectively, at zero. When the user initiates activities, a first type of movement occurs. This type of movement is referred to as "heel/toe" movement such as is exhibited in normal walking. That is, when taking a step, the user first plants the heel of the shoe, followed (in a rolling type of motion) by the sole of the shoe. This action, thus, initiates closure of switch 10 in the heel portion 11 of the bottom of the shoe 100, followed shortly by closure of switch 12.

Closure of either switch 10 or 12 causes a signal to be applied to the respective input of logic circuit 21. When the logic circuit detects an input signal from switch 10 followed shortly by a signal from switch 12, the logic circuit 21 supplies a signal to counter 23. For example, logic circuit 21 may include a one-shot circuit (not shown) which is activated for a prescribed time by closure of switch 10. The signal from the one-shot can be applied to an AND-gate. Activation of switch 12 causes another input signal to be applied to the AND-gate. The logic circuit thereby confirms that a step has been taken and the AND-gate then supplies a signal to counter 23 which then supplies a signal to the decoder/driver circuit 24. The decoder/driver circuit then supplies a signal to the step counter portion 50 of display 20. Thus, display 20 produces a counter of the number of steps taken by the wearer in the heel/toe step, (i.e walking— whether at normal or race-walking speed).

The step counter 50 counts consecutive steps by the user wherein a continuous count of the number of steps taken in these shoes by the user is obtained. The step counter 50 is constantly updated and, thereby, measures several parameters such as the life of the shoe, the steps taken, the miles walked and so forth. Of course, any such indication requires the proper calibration such as the length of step of the user, the expected life of the shoe, or the like.

Alternatively, when the user or wearer of the shoe 100 is running, the switch 10 is, generally, not activated after movement has begun. That is, in the running mode, only switch 12 is activated inasmuch as the wearer tends to run on the soles of the shoe—not the heel.

In this case, the AND-gate described supra is not utilized. Instead, the signals produced by pressure on switch 12 are supplied directly to the monitor 22. This circuit can operate on a suitable timer network which determines the frequency of the signals from switch 12. For example, comparators, time-out gates, or frequency timers can be used to establish the rate at which the signals are produced by activation of switch 12 alone.

The signal thus produced by monitor 22 is supplied to decoder/driver 24. The circuit 24 decodes the signals from monitor 22 and drives the speed indicator 40 portion of the display 20.

In the illustrative embodiment, the speed indicator comprises a bar graph display. It is, of course, recognized that other displays can be utilized. For example, a digital read out of the speed of the wearer of the shoe can be calculated and displayed.

The reset switch 25 is connected to monitor 22. The reset switch, which can be a pressure switch like switches 10 and 12, is used to reset the monitor 22 for a new or different measurement. The switch 25 can be placed at any suitable location on the shoe 100 so that the user/wearer of the shoe can selectively reset the circuit to zero (or some other initial condition).

The use of the circuitry shown in FIG. 2 transcends the need for an "off" attitude of the footwear to conserve battery power. The circuitry ensures only one momentary activation of the display upon closure of switch 10 or 12. This allows the shoe to be held or left in any attitude thereof without continuing illumination of the LCDs and the consequent battery power depletion.

Alternative arrangements are contemplated. For example, instead of being mounted in a pouch such as 14, the battery may also be encapsulated in the shoe material when using this circuitry. Although this effectively prevents battery replacement, it should be noted that, in many cases, the battery life will exceed the normal lifetime of the shoe.

Obviously, it is within the scope of the invention to use other circuits, integrated or otherwise, designed to be activated and to measure the stated parameters. Circuits to control the duration are of particular importance for the reasons previously explained.

Also, the display 20 can be placed elsewhere on the shoe such as is shown in phantom in FIG. 1. Alternatively, the display can be detachable wherein it is selectively connected to the circuit and information previously stored in a memory portion of decoder/driver circuit 24 is accessed.

Obviously, there is no limitation as to the types of footwear with which the invention may be used. Therefore, the footwear would include shoes, boots, overshoes, overboots, slippers, rubbers, or the like and whether designed for sports, fashion or utilitarian use.

Thus, there is shown and described a unique design and concept of a footwear which includes a step counter and a speedometer display. The particular configuration shown and described herein relates to an LCD display. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A monitored footwear comprising:

a circuit for selectively electrically monitoring steps taken by a wearer of said footwear;

a power source for supplying power to said circuit;

first and second pressure switches which alternate between "off" and "on" states in response to pressure thereon during steps taken by a wearer of said footwear;

said circuit includes logic circuit means for producing electrical signals as a function of the state of said first and second switches;

said logic circuit produces a first electrical signal only when said second pressure switch is in the "on" state shortly after said first pressure switch is in the "on" state, said first electrical signal is representative of a step having been taken by the wearer of said footwear, decoder means connected to said circuit and adapted to receive signals from said circuit and produce signals representative of said monitoring; and display means mounted on said footwear and connected to receive signals produced by said decoder means.

2. The footwear recited in claim 1 wherein, said circuit includes counting means connected to receive signals from said logic circuit means.

3. The footwear recited in claim 1 wherein, said display means is capable of displaying at least two different parameters.

4. The footwear recited in claim 1 including, a third switch connected to said circuit means and operative to selectively reset said circuit to a preselected condition.

5. The footwear recited in claim 1 wherein, said logic circuit produces a second electrical signal only when said first pressure switch is in the "on" state at least twice in a short period of time with no intervening "on" state at said second pressure switch.

6. The footwear recited in claim 5 wherein, said display means receives said second electrical signal and produces a display representative of the number of such second electrical signals received.

7. The footwear recited in claim 1 wherein, said display means receives said first electrical signal and produces a display representative of the number of such first electrical signals received.

* * * * *